United States Patent [19]

Lee et al.

[11] Patent Number: 5,608,094

[45] Date of Patent: Mar. 4, 1997

[54] BENZOSILACYCLOBUTENES AND METHODS OF MAKING

[75] Inventors: Chi-Long Lee, Midland, Mich.; Ming-Hsiung Yeh, New Freedom, Pa.

[73] Assignee: Dow Corning Corporation, Midland, Mich.

[21] Appl. No.: 539,008

[22] Filed: Oct. 4, 1995

[51] Int. Cl.$^6$ .................................................. C07F 7/08
[52] U.S. Cl. .................................... 556/406; 422/387
[58] Field of Search .......................... 556/406; 427/387

[56] References Cited

U.S. PATENT DOCUMENTS

| | | | |
|---|---|---|---|
| 4,985,565 | 1/1991 | Baney et al. | 556/406 X |
| 5,302,734 | 4/1994 | Jung et al. | 556/406 |

OTHER PUBLICATIONS

Journal of Organometallic Chemistry, 9 (1967), 251–257.

*Primary Examiner*—Paul F. Shaver
*Attorney, Agent, or Firm*—James L. DeCesare

[57] ABSTRACT

1,1-dimethyl-2,3-benzo-1-sila-2-cyclobutene was synthesized from 2-bromobenzyl bromide through a modified Grignard procedure, which resulted in a higher (41%) than literature reported yield (35%). An alternative approach with a much less costly 2-chlorobenzyl chloride as starting material is also disclosed. In addition, new di-benzosilacyclobutene compounds were synthesized with our modified Grignard procedure. The compounds are useful as coating materials for surfaces, and when applied to metallic surfaces, can be used neat.

19 Claims, No Drawings

BENZOSILACYCLOBUTENES AND METHODS OF MAKING

BACKGROUND OF THE INVENTION

This invention is directed to benzosilacyclobutenes and to methods of making them, including new di-benzosilacyclobutenes and to methods of making them.

In 1967, Eaborn, Walton, and Chan, reported in the Journal Of Organometallic Chemistry, 9(1967), 251–257, a method of making benzosilacycloalkenes by a route generally as follows:

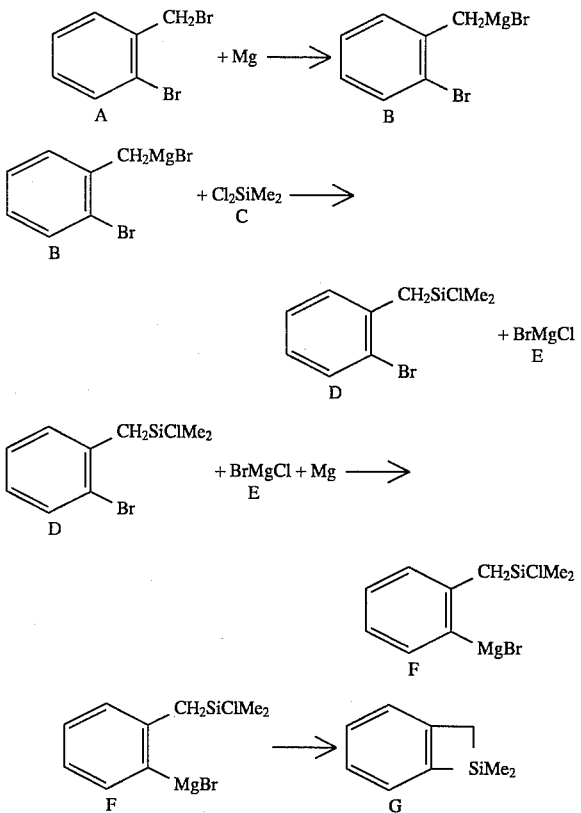

What we have done is to devise an improvement in that method, whereby we are able to achieve higher yields (i.e. 41%) than reported by Eaborn et al (i.e. 35%). In addition, new unreported di-benzosilacyclobutene compounds have been made, and methods of making those di-compounds have been devised.

SUMMARY OF THE INVENTION

It is therefore an object to provide an improved process with resultant higher yields for making benzosilacyclobutenes of the formula:

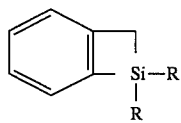

where R is an alkyl radical containing 1–6 carbon atoms such as methyl, ethyl, n-propyl, n-butyl, pentyl, and hexyl; or an aryl radical such as phenyl; provided one R is alkyl. Examples of compounds corresponding to the above formula are 1,1-dimethyl-2,3-benzo-1-sila-2-cyclobutene, and 1-methyl-1-phenyl-2,3-benzo-1-sila-2-cyclobutene.

It is another object to adapt the process for making benzosilacyclobutenes with 2-chlorobenzyl bromide as precursor for the Grignard reagent, instead of the traditional Grignard reagent precursor 2-bromobenzyl bromide.

In addition, it is a further object to provide new di-benzosilacyclobutene compounds and methods of making di-compounds of the formula:

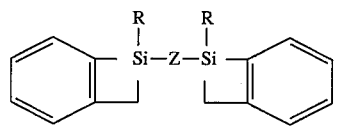

where R is as defined above; and Z is a divalent linking group composed of carbon and hydrogen atoms, with preferably no more than six carbon atoms, such as methylene, ethylene, propylene, and butylene.

These and other features of the invention will become apparent from a consideration of the detailed description.

DETAILED DESCRIPTION OF THE INVENTION

The Grignard synthesis can be illustrated simplistically as $RMgX+XSi\equiv \rightarrow RSi\equiv +MgX_2$. The function of the Grignard reagent RMgX is to substitute the organic group R for one or more chlorines on the silane $XSi\equiv$.

An aromatic halide precursor (A) is used to prepare the Grignard reagent (B) in situ by reacting the precursor with magnesium metal turnings in the presence of an ether solvent, i.e. $ArRX+Mg\rightarrow ArRMgX$. Typically, the solvent is a lower aliphatic ether such as diethyl ether, or a cyclic ether such as THF. Suitable aromatic halides useful as precursors are 2-bromobenzyl bromide and 2-chlorobenzyl chloride, for example. These precursors are used to form Grignard reagents benzylmagnesium bromide and benzylmagnesium chloride, respectively.

Aromatic halides combine slowly with magnesium, and it is customary to include an initiator. Compounds such as 1,2-dibromoethane can be used to initiate the reaction, which once started is exothermic, and may require external cooling to prevent loss of the ether. The reaction is carried out at a temperature in the range of 10°–150° C., preferably 40°–100° C., in an atmosphere of an inert gas such as nitrogen.

Preparation of the Grignard reagent is a surface reaction, and it can be enhanced, according to our invention, by including acid washed sand ($SiO_2$) to mechanically clean the magnesium surface. When accompanied with stirring, the acid washed sand buffs the magnesium surface, without buffing away reaction nuclei present on the surface.

Benzo-condensed four-member rings such as 1,1-dimethyl-2,3-benzo-1-sila-2-cyclobutene (G) can be prepared by reacting 2-bromobenzyl bromide with a mixture of magnesium and a diorganodihalosilane such as dimethyldichlorosilane (C). However, the product has been isolated at only about 35% yield, after hydrolysis to destroy excess Grignard reagent and consequent distillation. Generally, this procedure is tedious, and it is difficult to make the compounds in an efficient way. Thus, any slight improvement in the process or in its yield can be significant given its known difficulties.

According to our invention, we improved the Eaborn et al procedure which basically consists of in situ quenching the Grignard reagent, generated from magnesium and 2-bromobenzyl bromide in diethyl ether $CH_3CH_2OCH_2CH_3$, with dimethyldichlorosilane. Improvement in yield was achieved by two process modifications.

First, acid washed sand was introduced into the reaction flask to help clean the magnesium surface mechanically. An ultrasonic bath can be used to assist cleaning efficiency. The second modification was made by feeding a mixture of 2-bromobenzyl bromide, $Cl_2SiMe_2$, and 1,2-dibromoethane $BrCH_2CH_2Br$ as the initiator, into the magnesium/ether reaction mixture. This step is in contrast to literature procedures which use 1,2-dibromoethane in the initiation stage only. The continuous feeding of small amounts of 1,2-dibromoethane helps to reactivate the magnesium during the course of the reaction. According to our improved process, the isolated yield of 1,1-dimethyl-2,3-benzo-1-sila-2-cyclobutene after distillation was 41%, compared to no more than 35% yield reported by Eaborn et al.

We also discovered that 2-chlorobenzyl chloride could be used as Grignard reagent precursor instead of 2-bromobenzyl bromide, to synthesize 1,1-dimethyl-2,3-benzo-1-sila-2-cyclobutene via our modified process. To our knowledge, a successful synthesis using 2-chlorobenzyl chloride has not been previously reported.

2-chlorobenzyl chloride has advantages for a number of reasons. For example, (i) although 2-chlorobenzyl chloride is less reactive as a Grignard precursor, the generated benzylmagnesium chloride $C_6H_5CH_2MgCl$ Grignard reagent is less subject to coupling with benzylchloride; and (ii) a more efficient Grignard reagent solvent such as tetrahydrofuran (THF) is used instead of diethyl ether to achieve higher reaction temperatures. In addition, the cost of 2-chlorobenzyl chloride is only about 2% of the cost of 2-bromobenzyl bromide. The 1,1-dimethyl-2,3-benzo-1-sila-2-cyclobutene compound was prepared in THF from 2-chlorobenzyl chloride in a 23% isolated yield.

Organohalosilanes useful according to our invention include diorganodihalosilanes such as dialkyldihalosilanes; and diorganodihalosilanes containing alkyl and aryl groups, provided the diorganodihalosilane contains one alkyl group. Representative examples of some suitable organohalosilanes are:
dimethyldichlorosilane $(CH_3)_2SiCl_2$
ethylmethyldichlorosilane $CH_3(C_2H_5)SiCl_2$
diethyldichlorosilane $(C_2H_5)_2SiCl_2$
di-n-propyldichlorosilane $(n-C_3H_7)_2SiCl_2$
methylisopropyldichlorosilane $CH_3(i-C_3H_7)SiCl_2$
di-n-butyldichlorosilane $(n-C_4H_9)_2SiCl_2$
n-butylmethyldichlorosilane $CH_3(n-C_4H_9)SiCl_2$
amylmethyldichlorosilane $CH_3(C_5H_{11})SiCl_2$
di-n-hexyldichlorosilane $[(CH_3)(CH_2)_5]_2SiCl_2$
methylphenyldichlorosilane $CH_3(C_6H_5)SiCl_2$
phenylethyldichlorosilane $C_2H_5(C_6H_5)SiCl_2$ Our invention is further illustrated with reference to the following examples, in which the starting materials were purchased and used without further purification. The starting materials were employed in stoichiometric proportions. Infrared (IR) spectra were recorded on a Nicolet SX Fourier-transform Infrared spectrophotometer (FT-IR) using a KBr plate. Gas Chromatographic (GC) analyses were performed on a Hewlett-Packard HP 5890 capillary Gas Chromatograph. Gas Chromatograph/Mass Spectrometrics (GC/MS) were recorded with a Hewlett-Packard HP 5890/5971A GC/Mass Spectrometer. Ultraviolet (UV) spectra were recorded on a Bausch & Lomb Spectronic 2000 spectrophotometer in 0.5 cm quartz cells. Proton Nuclear Magnetic Resonance (NMR) was recorded on a Varian 200S in deuterated chloroform ($CDCl_3$). Gel Permeation Chromatography (GPC) was conducted on a Millipore 150C gel-packed column using toluene as mobile phase.

EXAMPLE I

Preparation of
1,1-dimethyl-2,3-benzo-1-sila-2-cyclobutene from
2-bromobenzyl bromide A four-necked flask equipped with a wire paddle mechanical stirrer, water-cooled condenser, addition funnel, and septum, was loaded with 15 g (0.62 g-atm) of magnesium turnings, 15 g of acid washed sand, and 45 ml of diethyl ether under nitrogen. About 0.25 g of 1,2-dibromoethane was added through the septum via a syringe into the magnesium/ether mixture. Once the magnesium was activated, a solution of 2-bromobenzyl bromide (33 g, 0.13 mole), dimethyldichlorosilane (18.2 g, 0.24 mole), and 1,2-dibromoethane (0.5 g) in 130 ml of diethyl ether was added dropwise through the addition funnel. The flask was heated such that a gentle refluxing of the ethereal mixture was maintained. The addition took 5 hours. After an additional 30 minutes of heating, the product mixture was cooled in an ice bath, and hydrolyzed with 200 ml of a 10% ammonium chloride aqueous solution to destroy excess Grignard reagent. The hydrolyzed mixture was filtered and the organic layer was separated. The organic layer was washed with 100 ml of water and dried over sodium sulfate. Removal of the solvent under reduced pressure afforded 17.9 g of a yellow liquid. Vacuum distillation (1.4 torr, b.p. 34°–39° C.) obtained 7.95 g (41% yield) of a water-clear liquid which was 100% pure via GC analysis: NMR (deuterated chloroform), delta (d) 5.89–6.17 (m, 4H), 0.95 (s, 2H), –0.75 (s, 6H); GC/MS (m/e), 148 (m+, 54%), 133 (100%), 105 (25%); UV (dodecane), lambda (l) max=267.9 nm, epsilon ($\Sigma$)=676. The liquid was 1,1-dimethyl-2,3-benzo-1-sila-2-cyclobutene:

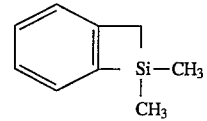

EXAMPLE II

Preparation of
1,1-dimethyl-2,3-benzo-1-sila-2-cyclobutene from
2-chlorobenzyl chloride Following the procedure in Example I, 10 g of magnesium turnings were mixed with 6.6 g of acid washed sand, and 50 ml of tetrahydrofuran. Once the magnesium was initiated by 1,2-dibromoethane, a mixture of 2-chlorobenzyl chloride (16.1 g, 0.1 mole), dimethyldichlorosilane (12 g, 0.093 mole), 1,2-dibromoethane (1 g), and tetrahydrofuran (130 ml), was added over a period of 1.5 hours, while the mixture was maintained at gentle refluxing under nitrogen. After an additional 6.5 hours of refluxing, the product mixture was hydrolyzed to destroy excess Grignard reagent. Following filtration, the aqueous layer was extracted with 50 ml of diethyl ether. The combined organic layer was washed with 100 ml of water and dried over sodium sulfate. Vacuum distillation obtained 3.1 g (23% yield) of water clear 1,1-dimethyl-2,3-benzo-1-sila-2-cyclobutene at 98.5% GC purity.

The following example illustrates another feature of our invention relating to a method for preparing di-benzosilacyclobutenes. According to our knowledge, di-benzosilacyclobutene compounds have not been synthesized previously. In this method, we used as quenching agent, a tetrahalodisilalkane compound of the formula $RX_2Si(CH_2)_nSiX_2R$ where R is a $C_1$–$C_6$ alkyl group, X is halogen, and n is 1–6. The particular compound used as quenching agent was 2,2,5,5-tetrachloro-2,5-disilahexane ($C_4H_{10}Cl_4Si_2$), and a di-benzosilacyclobutene was successfully synthesized. This quenching agent had the formula:

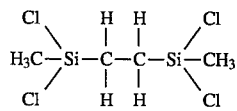

In this method, we found that while distillation was not an appropriate means of separation, even under high vacuum, reasonably pure materials could be obtained by extraction and washing of the product mixture without benefit of distillation.

EXAMPLE III

Preparation of
1,2-bis(1-methyl-2,3-benzo-1-sila-2-butenyl)ethane

A mixture of 10 g magnesium turnings (0.41 g-atm), acid washed sand (7 g), and diethyl ether (100 ml), was initiated with a small amount of 1,2-dibromoethane as described in Examples I and II. The compound 2,2,5,5-tetrachloro-2,5-disilahexane was made from the hydrosilation between methyldichlorosilane ($HMeSiCl_2$) and vinylmethyldichlorosilane ($H_2C=CHMeSiCl_2$). A solution of 2,2,5,5-tetrachloro-2,5-disilahexane (10.2 g, 0.04 mole); 2-bromobenzyl bromide (21 g, 0.084 mole); 1,2-dibromoethane (0.5 g); and diethyl ether (80 ml); was added dropwise into the magnesium/ether mixture at gentle refluxing temperature under nitrogen. The addition took 5 hours and an additional one hour of heating was applied. The product mixture was hydrolyzed in an ice bath to destroy excess Grignard reagent, and filtered. After washing with 50 ml water and drying with sodium sulfate, there was obtained 10.5 g of a liquid. GC, one peak only; GC/MS (m/e), 294 (m+, 100%), 279 (17%), 266 (26%), 251 (53%), 208 (45%), 203 (44%), 161 (4%), 133 (16%). The liquid was the compound:

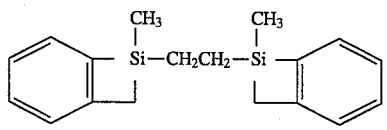

These benzosilacyclobutene and di-benzosilacyclobutene compounds are useful as coating materials. For example, they can be applied to a metal surface neat, and to other types of surfaces when mixed with an accelerator. Coatings can be formed at room temperature (20°–25° C./68°–77° F.), and no heat activation is required. Surfaces which can be coated neat with these benzosilacyclobutene and di-benzosilacyclobutene compounds are, for example, iron, platinum, copper, and zinc surfaces. Other surfaces require the addition of 1–20% by weight, preferably about 10% by weight, of an accelerator. Useful accelerators are metal or metal compounds such as iron, ferric chloride ($FeCl_3$), platinum, platinum dichloride ($PtCl_2$), copper, cupric chloride ($CuCl_2$), and zinc chloride ($ZnCl_2$).

Both the benzosilacyclobutene and di-benzosilacyclobutene compounds were tested as coatings. The coating test was performed by mixing an accelerator with a benzosilacyclobutene or di-benzosilacyclobutene compound in an open vessel, or by applying a thin coating of the benzosilacyclobutene or di-benzosilacyclobutene compound on a metal surface. Hard coatings were formed in a matter of minutes (i.e. 20–30 minutes), and in some cases a few hours (i.e. 1–3 hours), depending upon the effectiveness of the surface contact.

We determined that the best results could be obtained by making thin coatings of the benzosilacyclobutene and di-benzosilacyclobutene compounds on a metal surface, or by mixing those compounds with a powdered accelerator under fast stirring conditions. For example, we applied 1,1-dimethyl-2,3-benzo-1-sila-2-cyclobutene as a thin coating on top of a copper plate at room temperature, and a white coating formed almost immediately.

Some practical applications of these benzosilacyclobutene and di-benzosilacyclobutene compounds as coatings are their use on pipe joints, as thread seals, and electronic encapsulation.

Other variations and modifications may be made in the compounds and methods described without departing from the essential features of the invention. The forms of invention are exemplary and not limitations on the scope of the invention defined in the claims.

That which is claimed is:

1. A method of making benzosilacyclobutenes comprising forming a mixture of magnesium, acid washed sand, a solvent, and a reaction initiator; once the magnesium is activated, continuously adding to the mixture a solvent solution of an aromatic halide as a Grignard reagent precursor, a diorganodihalosilane, and a second portion of the reaction initiator; heating the mixture to maintain a temperature of 10°–150° C.; thereafter separating and recovering a benzosilacyclobutene compound from the mixture.

2. A method according to claim 1 in which the Grignard reagent precursor is 2-bromobenzyl bromide or 2-chlorobenzyl chloride.

3. A method according to claim 2 in which the diorganodihalosilane is a dialkyldihalosilane or a diorganodihalosilane containing alkyl and aryl groups provided the diorganodihalosilane contains one alkyl group.

4. A method according to claim 3 in which the solvent is diethyl ether or tetrahydrofuran.

5. A method according to claim 4 in which the reaction initiator is 1,2-dibromoethane.

6. A method according to claim 1 in which the benzosilacyclobutene compound has the formula:

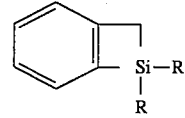

where R is an alkyl radical containing 1–6 carbon atoms or an aryl radical provided one R is alkyl.

7. A method according to claim 6 in which the benzosilacyclobutene compound is 1,1-dimethyl-2,3-benzo-1-sila-2-cyclobutene or 1-methyl-1-phenyl-2,3-benzo-1-sila-2-cyclobutene.

8. A method of making di-benzosilacyclobutenes comprising forming a mixture of magnesium, acid washed sand, a solvent, and a reaction initiator; once the magnesium is activated, continuously adding to the mixture a solvent solution of an aromatic halide as a Grignard reagent precursor, a tetrahalodisilalkane, and a second portion of the reaction initiator; heating the mixture to maintain a temperature of 10°–150° C.; thereafter separating and recovering a di-benzosilacyclobutene compound from the mixture.

9. A method according to claim 8 in which the Grignard reagent precursor is 2-bromobenzyl bromide or 2-chlorobenzyl chloride.

10. A method according to claim 9 in which the tetrahalodisilalkane is 2,2,5,5-tetrachloro-2,5-disilahexane.

11. A method according to claim 10 in which the solvent is diethyl ether or tetrahydrofuran.

12. A method according to claim 11 in which the reaction initiator is 1,2-dibromoethane.

13. A method according to claim 8 in which the compound has the formula:

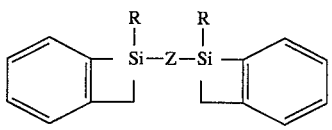

where R is an alkyl radical containing 1–6 carbon atoms or an aryl radical provided one R is alkyl; and Z is a divalent linking group composed of carbon and hydrogen atoms.

14. A method according to claim 13 in which the compound is:

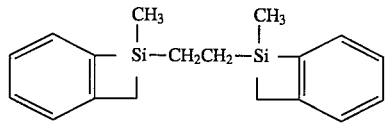

15. Compounds of the formula:

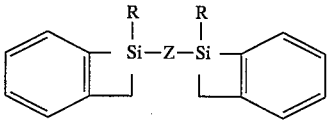

where R is an alkyl radical containing 1–6 carbon atoms or an aryl radical provided one R is alkyl; and Z is a divalent linking group composed of carbon and hydrogen atoms.

16. A compound of the formula:

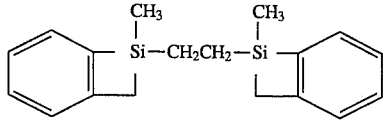

17. A composition comprising (i) an accelerator selected from the group consisting of iron, ferric chloride, platinum, platinum dichloride, copper, cupric chloride, and zinc chloride; and (ii) a benzosilacyclobutene or di-benzosilacyclobutene compound of the formula:

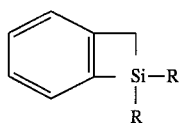

or the formula:

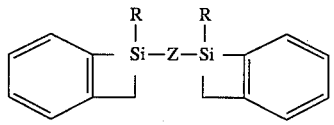

respectively, where R in each formula is an alkyl radical containing 1–6 carbon atoms or an aryl radical; and Z is a divalent linking group composed of carbon and hydrogen atoms; provided one R in each formula is alkyl.

18. A method of coating a surface comprising applying to the surface a composition comprising (i) an accelerator selected from the group consisting of iron, ferric chloride, platinum, platinum dichloride, copper, cupric chloride, and zinc chloride; and (ii) a benzosilacyclobutene or di-benzosilacyclobutene compound of the formula:

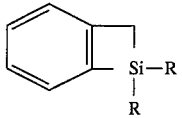

or the formula:

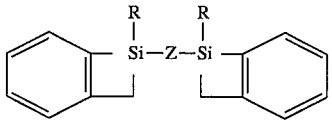

respectively, where R in each formula is an alkyl radical containing 1–6 carbon atoms or an aryl radical; and Z is a divalent linking group composed of carbon and hydrogen atoms; provided one R in each formula is alkyl.

19. A method of coating an iron, platinum, copper, or zinc surface comprising applying to iron, platinum, copper, or zinc surfaces, a benzosilacyclobutene or di-benzosilacyclobutene compound of the formula:

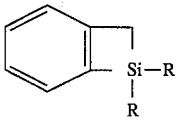

or the formula:

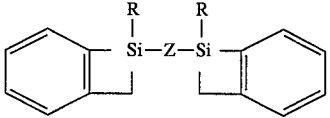

respectively, where R in each formula is an alkyl radical containing 1–6 carbon atoms or an aryl radical; and Z is a divalent linking group composed of carbon and hydrogen atoms; provided one R in each formula is alkyl.

* * * * *